US007048733B2

(12) United States Patent
Hartley et al.

(10) Patent No.: US 7,048,733 B2
(45) Date of Patent: *May 23, 2006

(54) SURGICAL PERFORATION DEVICE WITH CURVE

(75) Inventors: Amanda April Hartley, Brampton (CA); Krishan Shah, Mississauga (CA); Naheed Visram, Markham (CA); Frank Baylis, Beaconsfield (CA)

(73) Assignee: Baylis Medical Company Inc., Mississauga (CA)

( * ) Notice: Subject to any disclaimer, the term of this patent is extended or adjusted under 35 U.S.C. 154(b) by 6 days.

This patent is subject to a terminal disclaimer.

(21) Appl. No.: 10/666,301

(22) Filed: Sep. 19, 2003

(65) Prior Publication Data

US 2005/0065507 A1 Mar. 24, 2005

(51) Int. Cl.
*A61B 18/18* (2006.01)
(52) U.S. Cl. .................. 606/41; 607/101; 607/122
(58) Field of Classification Search .......... 606/1–50; 607/96–101, 122; 600/485–488
See application file for complete search history.

(56) References Cited

U.S. PATENT DOCUMENTS

| | | | |
|---|---|---|---|
| 3,448,739 A | 6/1969 | Stark et al. | |
| 4,682,596 A | 7/1987 | Bales et al. | |
| 4,928,693 A | 5/1990 | Goodin et al. | |
| 4,936,281 A | 6/1990 | Stasz | |
| 5,098,431 A | 3/1992 | Rydell | |
| 5,281,216 A | 1/1994 | Klicek | |
| 5,364,393 A | 11/1994 | Auth et al. | |
| 5,403,338 A | 4/1995 | Milo | |
| 5,545,200 A * | 8/1996 | West et al. | 607/122 |
| 5,673,695 A * | 10/1997 | McGee et al. | 600/374 |
| 5,683,366 A | 11/1997 | Eggers et al. | |
| 5,814,028 A * | 9/1998 | Swartz et al. | 604/528 |
| 5,904,679 A | 5/1999 | Clayman | |
| 5,921,957 A | 7/1999 | Killion et al. | |

(Continued)

FOREIGN PATENT DOCUMENTS

EP 0315730 5/1989

(Continued)

OTHER PUBLICATIONS

Lee N. Benson, David Nykanen, Amanda Collison. "Radiofrequency Perforation in the Treatment of Congenital Heart Disease". Catheterization and Cardiovascular Interventions. 56: 72-82 (2002).

(Continued)

*Primary Examiner*—Michael Peffley
(74) *Attorney, Agent, or Firm*—Ogilvy Renault LLP (57) ABSTRACT

A device for creating a surgical perforation with a functional distal tip for creating a controlled perforation. The functional tip may comprise at least one active electrode for creating the perforation through the application of Radio Frequency (RF) energy. The device is curved in order to decrease the likelihood of injury to structures of a patient such as inadvertent cardiac perforation when used in transseptal perforation procedures. The device is introduced into the right atrium, and the functional tip is then positioned against the atrial septum. Energy is applied to create the perforation. The tip is advanced toward the left atrium to create the perforation and as it advances into the left atrium, the device takes on its curved shape to direct the tip away from cardiac structures. The position of the tip of the device can be determined in response to pressure sensed at the tip and determined by a monitor.

8 Claims, 11 Drawing Sheets

U.S. PATENT DOCUMENTS

| | | | |
|---|---|---|---|
| 6,146,380 A * | 11/2000 | Racz et al. | 606/41 |
| 6,293,945 B1 | 9/2001 | Parins et al. | |
| 6,296,615 B1 | 10/2001 | Brockway et al. | |
| 6,565,562 B1 * | 5/2003 | Shah et al. | 606/41 |
| 6,632,222 B1 * | 10/2003 | Edwards et al. | 606/41 |
| 6,650,923 B1 | 11/2003 | Lesh et al. | |
| 6,811,544 B1 | 11/2004 | Schaer | |
| 6,814,733 B1 | 11/2004 | Leatham et al. | |
| 2002/0087156 A1 * | 7/2002 | Maguire et al. | 606/41 |
| 2002/0111618 A1 * | 8/2002 | Stewart et al. | 606/41 |
| 2002/0123749 A1 * | 9/2002 | Jain | 606/41 |
| 2002/0169377 A1 | 11/2002 | Khairkhahan et al. | |

FOREIGN PATENT DOCUMENTS

| | | |
|---|---|---|
| WO | WO-9320747 | 10/1993 |
| WO | WO 2004/039433 A2 | 5/2004 |

OTHER PUBLICATIONS

C.R. Conti. "Transseptal Left Heart Catheterization for Radiofrequency Ablation of Accessory Pathways". Clin. Cardiol. 16, 367-368 (1993).

Gideon J. Du Marchie Sarvaas, Kalyani R. Trivedi, Lisa K. Hornberger, K. Jin Lee, Joel A. Kirsh, Lee N. Benson. "Radiofrequency-Assisted Atrial Septoplasty for an Intact Atrial Septum in Complex Congenital Heart Disease". Catheterization and Cardiovascular Interventions. 56: 412-415 (2002).

Kamal K. Sethi, Jagdish C. Mohan. "Editorial Comment: Transseptal Catheterization for the Electrophysiologist: Modification with a 'View'". Journal of Interventional Cardiac Physiology. 5, 97-99, 2001.

Christodoulos Stefanadis. "Retrograde Nontransseptal Balloon Mitral Valvuloplasty: Immediate Results and Intermediate Long-Term Outcome in 441 Cases—A Multicentre Experience". Journal of the American college of Cardiology. 32(4): 1009-16 (1998).

CA Pedra, LN De Sousa, SR Pedra, WP Ferreira, SL Braga, CA Esteves, MV Santant, JE Sousa, VF Fontes. "New Percutaneous techniques for perforation the pulmonary valve in pulmonary atresia with intact ventricular septum". Arq Bras Cariol. 77(5):471-48 (2001).

DG Nykanen, J Phikala, GP Taylor, LN Benson. "Radiofrequency assisted perforation of the atrial septum in a swine model: feasibility, biophysical and histological characteristics". Circulation. 100(Suppl 1):1-804 (1999).

Baylis Medical Company Inc. "Radio Frequency Perforation System". (2001).

"ABSTRACT of European Patent No. 0315730 to Osypka". (1989).

Boston Scientific Corporation. "http://www.bostonscientific.com/med_specialty/deviceDetail.jsp?task=tskBasicDevice.jsp&sectionid=4&relId=1,20,21,22&deviceid=488&uniqueID=MPDB58". Explorer ST Catheters. 2 pages. (Date or printing—Jun., 2005).

Boston Scientific Corporation "http://www.bostonscientific.com/med_specialty/deviceDetail.jsp?task=tskBasicDevice.jsp&sectionId=4&relId=2,74,75,76&deviceId=556&uniqueID=MPDB4320". Impulse Angiographic Catheter. 2 pages (Date of printing—Jun., 2005).

Boston Scientific Corporation "http://www.bostonscientific.com/med_specialty/deviceDetail.jsp?task=tskBasicDevice.jsp&sectionId=4&relId=2,74,75,76&deviceId=11026&uniqueID=MPDB2799". PT2 Guide Wire. 2 pages (Date of printing—Jun., 2005).

IntraLuminal Therapeutics, Inc. "http://www.intraluminal.com/products/catheter.html". Safe Cross Support Catheter. 1 page. (Date of printing—Jun., 2005).

Lake Region Manufacturing, Inc. "http://www.lakergn.com/jmc.htm". Paragon Guidewire. 2 pages. (Date of printing—Jun., 2005).

Medtronic Inc. "http://www.medtronic.com/epsystems/diagnostic_catheters.html". Diagnostic Catheters. 7 pages. (Date of printing—Apr., 2005).

Johnson & Johnson Gateway, LLC. "http://www.jnjgateway.com/home.jhtml?loc=USENG& page=viewContent&contentId=Ic0de00100001435&nodekey=/Prod_info/Specialty/Arrhythmia_Management/Electrophysiology/EP_Diagnostic_Catheters". EP Diagnostic Catheters, 2 pages (Date of printing—Jun., 2005).

Johnson & Johnson Gateway, LLC. "http://www.jnjgateway.com/home.jhtml;jsessionid=JNSFHTWOAOIC0CQPCCE-CPJYKB2IIWNSC?icc=USENG&page=viewContent&contentid=IC0de00100000524&nodekey=/Prod_Info/Specialty/Cardiovascular_and_Thoracic/Cardiac_Diagnosis_Interventions/Diagnostic_Wires&_requestid=228905", Diagnostic Guidewires, 4 pages, (Date of Printing—Jun., 2005).

H Justino, LN Benson, DG Nykanen. "Transcatheter Creation of an Atrial Septal Defect Using Radiofrequency Perforation". Catheter Cardiovasc Interv. 54(1):83-87 (Sep. 2001).

N Shimko, P. Savard, K Shah. "Radio frequency perforation of cardiac tissue: modeling and experimental results". Med. Biol. Eng. Comput. 38:575-582 (2000).

T Abdel-Massih, Y Boudjemline, P Bonhoeffer. "Unusual Interventional management in an adult with tetralogy of Fallot". Cardiol Young. 13(2):203-205 (Apr., 2003).

T Humpl, B Soderberg, BW McCrindle, DG Nykanen, RM Freedom, WG Williams, LN Benson. "Percutaneous balloon valvotomy in pulmonary atresia with intact ventricular septum; impact on patient care", Circulation. 108(7):826-832 (Aug., 2003).

CA Pedra, RM Filho, RS Arrieta, R. Tellez, VF Fontes. "Recanalization of a discrete atretic right pulmonary artery segment with a new radiofrequency system". Catheter Cardiovasc Interv. 60(1):82-87 (Sep., 2003).

HW Kort, DT Balzer. "Radiofrequency perforation in the treatment of acquired left pulmonary atresia following repair of teraligy of Fallot". Catheter Cardiovasc Interv. 60(1):79-81 (Sep., 2003).

G Veldtman, A Peirone, LN Benson. "Radiofrequency perforation of the atrial septum: Preliminary experimental evaluation and development." PICS VII Abstracts. Catheter Cardiovasc Interv. 60(1):132 (Sep., 2003).

F Godart, C Francart, GM Breviere, C Rey. "Pulmonary vavulotomy with the Nykanen radiofrequency guide in pulmonary atresia with intact interventricular septum", Arch Mal Coeur Vaiss. 96(5):517-520 (May, 2003), Article is in French with an English summary.

* cited by examiner

SURGICAL PERFORATION DEVICE WITH CURVE

TECHNICAL FIELD

The invention relates to a device for creating a perforation in material of a patient such as the septum of the heart. More specifically, the invention relates to a device for creating a perforation in the material while minimizing the risk of inadvertent injury to other patient structures.

BACKGROUND OF THE ART

It is often required to create a perforation in the atrial septum to gain access to the left side of the heart interventionally to study or treat electrical or morphological abnormalities. It is also often desirable to create a hole in the atrial septum in patients with congenital heart defects in order to shunt the blood flow between the left and right sides of the heart to relieve high pressure or provide more blood flow to certain areas. Historically in these instances, a needle such as the Transseptal needle set of Cook Incorporated, Bloomington, Ind., USA is used. The needle is made of a stiff metal cannula, and has a sharpened distal tip. The needle is introduced through a guiding sheath in the femoral vein and advanced through the vasculature into the right atrium. From there the needle tip is positioned at the fossa ovalis, the preferred location on the septum for creating a perforation. Once in position, the operator applies force at the proximal end of the needle and uses mechanical energy to advance the needle through the septum and into the left atrium. Once in the left atrium the needle can be attached to an external pressure transducer and the operator can confirm a left atrial pressure before continuing with the procedure. Examples of subsequent steps may include advancing the guiding sheath over the needle and into the left atrium to provide access for other devices to the left heart, or using another device to enlarge the hole made by the needle if a shunt is desired.

This method of creating a transseptal perforation relies on the skill of the operator and requires practice to be performed successfully (Sethi et al, 2001). The needles used in this procedure are very stiff and can damage the vessel walls as they are being advanced. In addition, the amount of force required to perforate the septum varies with each patient. The force applied by the needle usually causes the septum to tent, or buckle, before it perforates the tissue. Once the needle makes the perforation, the needle may have significant forward momentum, which can be difficult to control. If too much force is applied there is the possibility of the needle perforating the septum and continuing to advance so far that damage is done to other areas of the heart. C. R. Conti (1993) discusses this possibility, and states that if the operator is not careful, the posterior wall of the heart can be punctured by the needle when it crosses the atrial septum because of the proximity of the two structures. Unintentional cardiac perforation has been shown in a number of studies to be a real concern during transseptal procedures, with incidence rates up to 6.7% (Stefanadis et al 1998, Sethi et al 2001).

U.S. Pat. No. 6,565,562 "Method for the radio frequency perforation and the enlargement of a body tissue" issued to Shah et al. describes a method of perforating tissue such as an atrial septum using a radiofrequency (RF) perforating device. A functional tip on the RF perforating device is placed against target tissue and as RF current is applied a perforation is created. This method allows a perforation to be created without applying significant force that causes the tissue to tent and the RF perforating device easily passes through the tissue. However, even with this method there is danger of causing unwanted injury to other areas of the heart because the perforating device can be advanced too far unknowingly while RF current is being applied.

Patients requiring transseptal punctures would benefit from a device that decreases the risk of unwanted injury, which may include inadvertent puncture, perforation, laceration, or damage to cardiac structures. In particular, patients with a muscular septum, as well as those with a thick septum can benefit from an alternative to the transseptal needle puncture (Benson et al, 2002), as it is difficult to control the amount of mechanical force required to create the puncture. Furthermore, children born with heart defects such as hypoplastic left heart syndrome could benefit from an alternative technique. The abnormal anatomy of these patients including a small left atrium increases the likelihood of injury or laceration of surrounding structures during transseptal puncture (Sarvaas, 2002).

A solution to one or more of these shortcomings is therefore desired.

SUMMARY OF THE INVENTION

The invention provides a surgical device for creating a perforation in material of a patient, including in particular, material that comprises the interatrial septum. The invention seeks to provide a device that is associated with a decreased risk of unintentional injury to other areas of the heart.

In accordance with the invention, there is provided a device for creating a perforation in material within a patient. The device comprises an elongate member having a proximal region and a distal region capable of adopting a curved shape; and a functional tip at the distal region for delivering energy to create the perforation in the material. When the functional tip advances through the material, the distal region adopts a curved shape to direct the functional tip in a desired direction. The material may comprise a body tissue, for example the atrial septum of a heart. A feature of the invention is that the curved shape may be defined by a radial arc and a further feature of the proximal region includes a marking indicative of the orientation of the curved shape.

In accordance with a further aspect, the invention provides a device for creating a perforation in a heart septum. The device comprises an elongate member having a proximal region and a distal region capable of adopting a curved shape; and a functional tip at the distal region for delivering energy to create the perforation in the septum. When the functional tip advances through the septum, the distal region adopts a curved shape to direct the functional tip in a desired direction. The curved shape may be defined by a radial arc and the functional tip may be directed away from cardiac structures. In particular, the functional tip is directed away from cardiac structures in order to decrease the risk of unwanted injury.

Preferably, the proximal region comprises a marking indicative of the orientation of the curved shape.

As a feature of this aspect, when the energy form is mechanical, the functional tip comprises a sharp tip. In such a case, the portion of the distal region defining the curved shape may be made of a super-elastic metal.

However, the energy may be at least one form of energy selected from a group consisting of: electrical current; microwave; ultrasound; mechanical; and laser. When the energy is electrical current, it may have a frequency within the radio frequency (RF) range. When the electrical current energy is in the RF range, it may be applied to ionize a conductive medium on top of a target tissue resulting in a low temperature molecular disintegration.

When the energy form is electrical, the functional tip may comprise at least one active electrode. Further the functional tip may comprise two or more electrodes and the electrodes may be configured in an arrangement where at least one of the electrodes is active and at least one is a return electrode.

As a feature of this aspect, the device may comprise a pressure sensing mechanism associated with the distal region for monitoring pressure about the distal region. The pressure sensing mechanism may comprise a pressure transmitting lumen extending between the proximal and distal regions. The lumen is adapted at the proximal region for fluid communication with a pressure transducer and adapted at the distal region for fluid communication with an environment about the distal region. Preferably, the distal region defines at least one opening to the environment such that the lumen is in fluid communication with the at least one opening. Optionally, the pressure sensing mechanism comprises a pressure transducer on-board the distal region, the transducer being adapted for communication with a pressure monitoring system.

Thus, the invention relates to a transseptal device configured for decreasing the likelihood of unintentional cardiac injury. The device may comprise a curve at the distal end of the device. The curved region at the distal end of the device is made of an elastic material such that the distal end of the device conforms to an internal lumen of a guiding catheter in order to be advanced through the guiding catheter within the vasculature. The distal end of the device remains inside the guiding catheter while the functional tip is exposed and then positioned against the desired perforation location on the septum. This ensures that the device remains straight while it is being positioned and during perforation. Once the device has perforated the septum, it is advanced out of the guiding catheter and through the perforation. This allows the distal end to take on its natural curve within the left atrium. As a result of the curve the functional tip does not continue to move forward towards the posterior wall of the heart. The functional tip is positioned at the end of the curve, and is unlikely to inadvertently injure other structures within the heart. If the operator inadvertently advances the device beyond the desired location, the curved portion of the device, instead of the functional tip, would contact the posterior wall of the heart. The curved portion is constructed of a material that is unlikely to cause any damage to heart structures.

It is to be understood that references to perforate or perforating a material, such as tissue, in relation to the present invention includes puncturing, cutting, ablating, coagulating and removing material.

DESCRIPTION OF THE DRAWINGS

In order that the invention may be readily understood, embodiments of the invention are illustrated by way of examples in the accompanying drawings, in which.

It will be noted that throughout the appended drawings, like features are identified by like reference numerals.

DETAILED DESCRIPTION OF THE INVENTION

Figure 1:
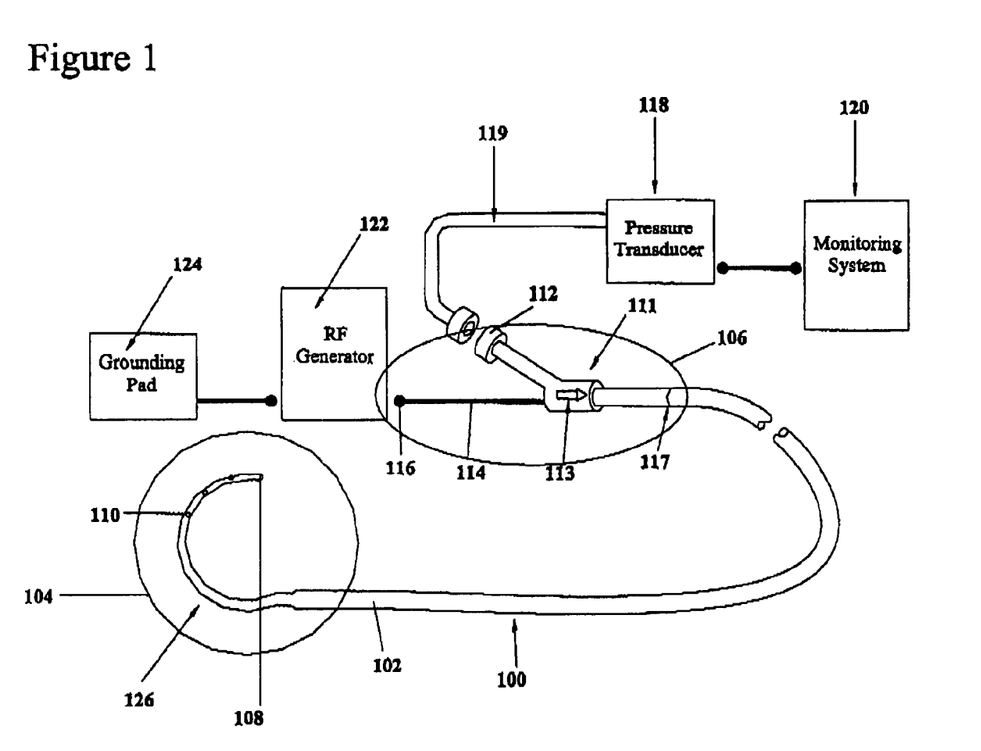
FIG. 1 illustrates a schematic view of an electrosurgical system including a preferred embodiment of a transseptal device in accordance with the invention.

FIG. 1 illustrates a preferred embodiment of a transseptal device 100 in accordance with the invention. Transseptal device 100 comprises an elongate member 102 having a distal region 104, and a proximal region 106. The Distal region 104 is adapted to be inserted within and along a lumen of a body of a patient, such as a patient's vasculature, and maneuverable therethrough to a desired location proximate to septal tissue to be cut.

The elongate member 102 is typically tubular in configuration, having at least one lumen extending from the proximal region 106 to the distal region 104. Elongate member 102 is preferably constructed of a biocompatible polymer material that provides column strength. The elongate member 102 is sufficiently stiff to permit a soft guiding catheter to be easily advanced over the transseptal device 100 and through a perforation. Examples of suitable materials for the tubular portion of elongate member 102 are polyetheretherketone (PEEK), and polyimide. In a preferred embodiment, the outer diameter of the tubular portion of elongate member 102 tapers down to connect to the distal region 104. In alternate embodiments the outer diameter of the elongate member 102 and the outer diameter of distal region 104 are the same.

The distal region 104 comprises a functional tip 108. A preferred embodiment of the functional tip 108 comprises at least one active electrode made of an electrically conductive and radiopaque material, such as stainless steel, tungsten, platinum, or another metal. Distal region 104 defines at least one opening 110 in fluid communication with a main lumen as described further below. Radiopaque markers (not shown) may be affixed to the elongate member 102 to highlight the location of the transition from the distal region 104 to the elongate member 102, or other important landmarks on the transseptal device 100 such as locations of openings 110.

The distal region 104 is constructed of a softer polymer material than the proximal region 106 so that it is pliable and atraumatic when advanced through vasculature. The material is also formable, so that its shape can be changed during manufacturing, typically by exposing it to heat while it is fixed in a desired shape. In an alternate embodiment, the shape of distal region is modifiable by the operator during use. An example of a suitable material is Pebax (a registered trademark of Atofina Chemicals, Inc.). The distal region 104 comprises a curve 126 such that the distal region 104 curls up inside a patient's left atrium as the functional tip 108 crosses the patient's atrial septum. This ensures that functional tip 108 is not in a position to inadvertently injure unwanted areas within a patient's heart after septal perforation. The curve is further described in following paragraphs. Distal region 104 preferably has a smaller outer diameter than elongate member 102 so that dilation of a perforation is limited while the distal region 104 is advanced through the perforation. Limiting dilation ensures that the perforation will not cause hemodynamic instability once the transseptal device 100 is removed. The outer diameter of distal region 104 will preferably be no larger than 0.035" (0.897 mm). This is comparable to the distal outer diameter of the transseptal needle that is traditionally used for creating a perforation in atrial septums. The elongate member 102 has a diameter preferably no larger than 0.050" (1.282 mm), which is also comparable to the transseptal needle dimensions.

The proximal region 106 comprises a handle 111, a hub 112, a cable 114, and a connector 116. The proximal region 106 may also have one or more markings 117 to indicate distances from functional tip 108, or other important landmarks on the transseptal device 100. Handle 111 comprises a curve direction or orientation indicator 113 that is located on the same side of the transseptal device 100 as the curve 126 in order to indicate the direction of the curve 126. Orientation indicator 113 may comprise inks, etching, or other materials that enhance visualization or tactile sensation. Persons of ordinary skill in the art will appreciate that one or more curve direction indicators may be used and that they may be of any suitable shape and size and a location thereof may be varied about the proximal region 106.

The hub 112 is configured to releaseably couple the transseptal device 100 to an external pressure transducer 118 via external tubing 119. The pressure transducer 118 is coupled to a monitoring system 120 that converts a pressure signal from the pressure transducer 118 and displays pressure as a function of time. Cable 114 is coupled to the connector 116, which is used to releaseably couple the transseptal device 100 to an energy source such as a generator 122.

The generator 122 is preferably a radiofrequency (RF) electrical generator that is designed to work in a high impedance range. Because of the small size of the functional tip 108, impedance encountered during RF energy application is very high. General electrosurgical generators are typically not designed to deliver energy in this impedance range, so only appropriate RF generators can be used with this transseptal device 100. In the preferred embodiment, energy is delivered as a continuous wave at a frequency between about 400 kHz and about 550 kHz. An appropriate generator for this application is the BMC RF Perforation Generator (model number RFP-100, Baylis Medical Company, Montreal, Canada). This generator delivers continuous RF energy at about 460 kHz. A grounding pad 124 is coupled to the generator 122 for attaching to a patient to provide a return path for the RF energy. Other embodiments could use pulsed or non-continuous RF energy, or using RF energy to ionize a conductive medium on top of the target tissue resulting in a low temperature molecular disintegration. This is sometimes referred to as, Coblation (registered trademark of Arthrocare Corporation, Sunnyvale, Calif.). In still other embodiments of the invention, different energy sources may be used, such as microwave, ultrasound, and laser, with appropriate energy delivery coupling devices.

Figure 2:
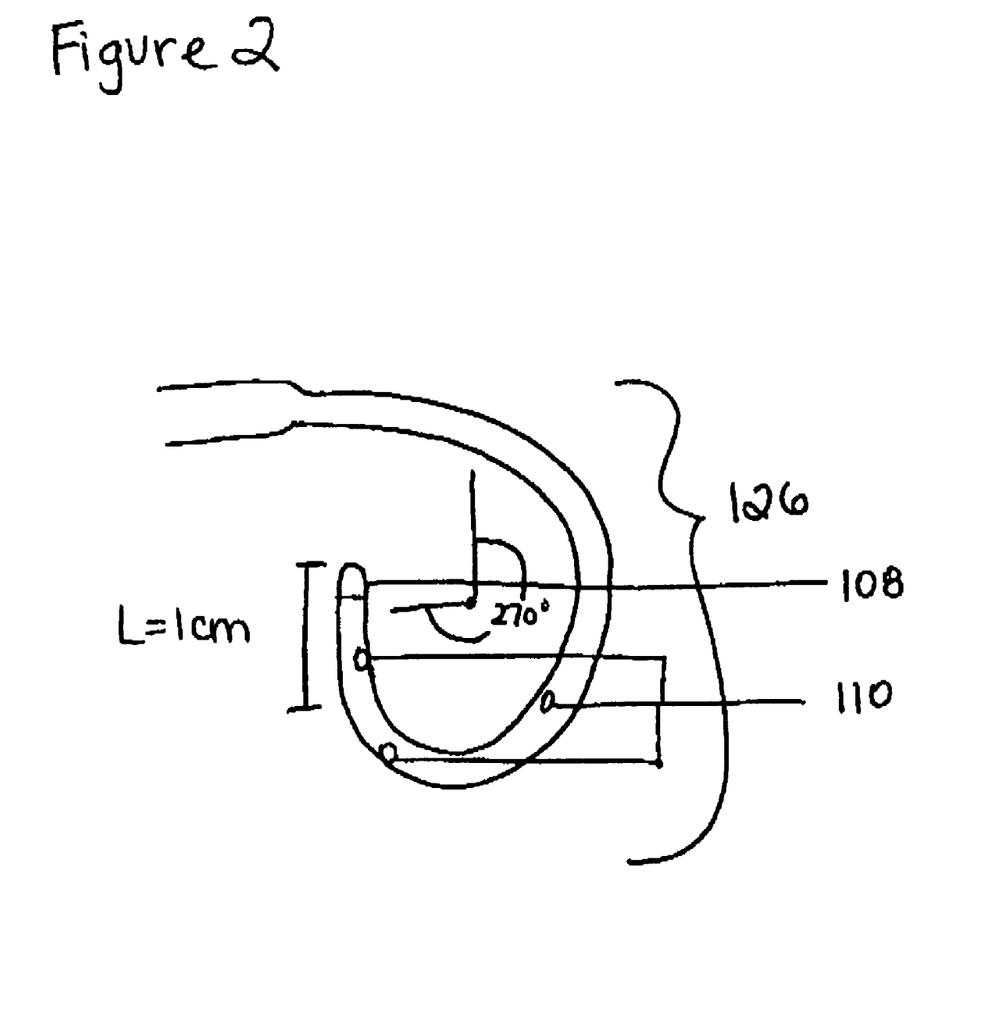
FIG. 2 illustrates the curve of the transseptal device of FIG. 1.
Figure 3:
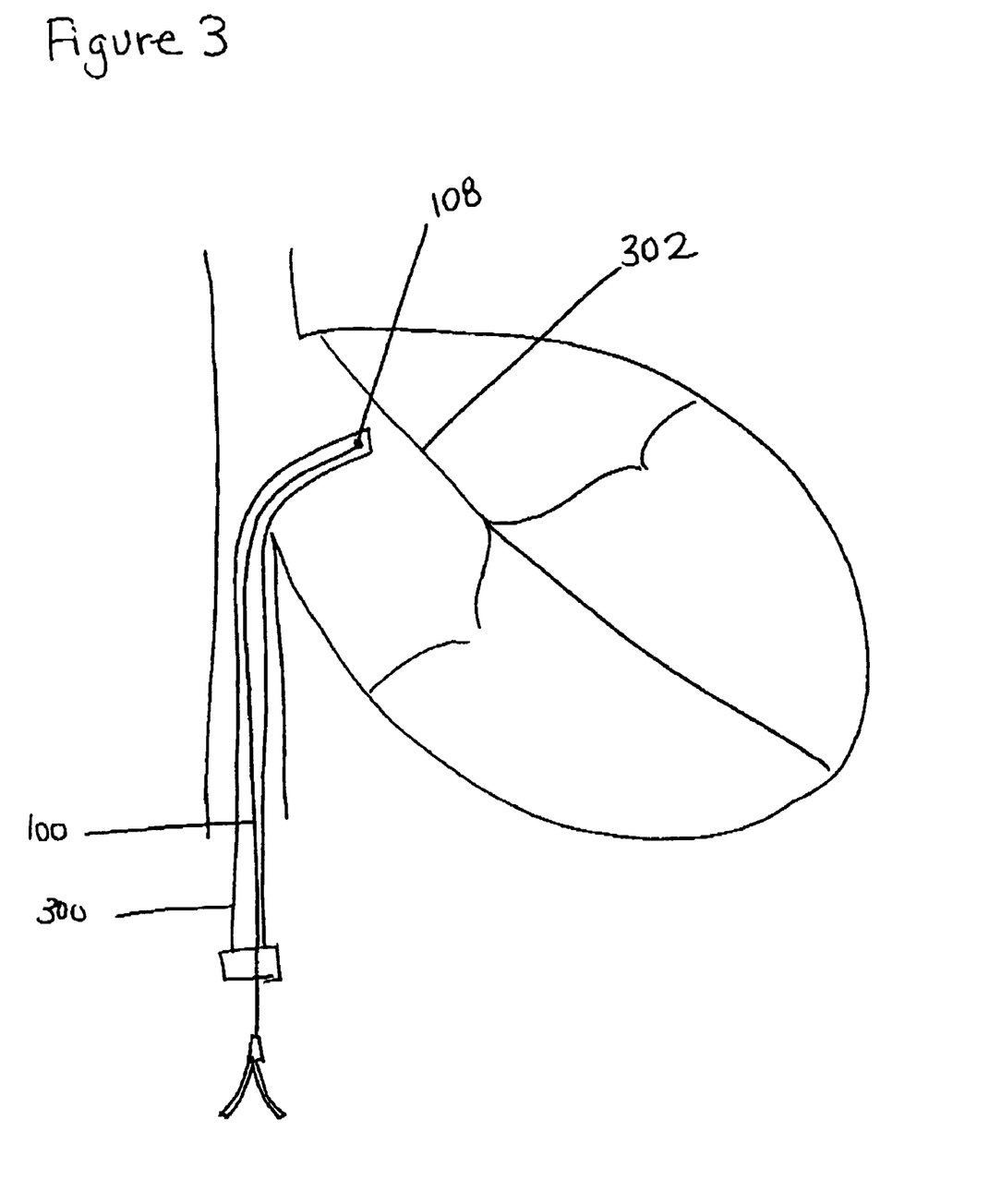
FIG. 3 illustrates a view of the device of FIG. 1 positioned inside a guiding catheter.
Figure 4:
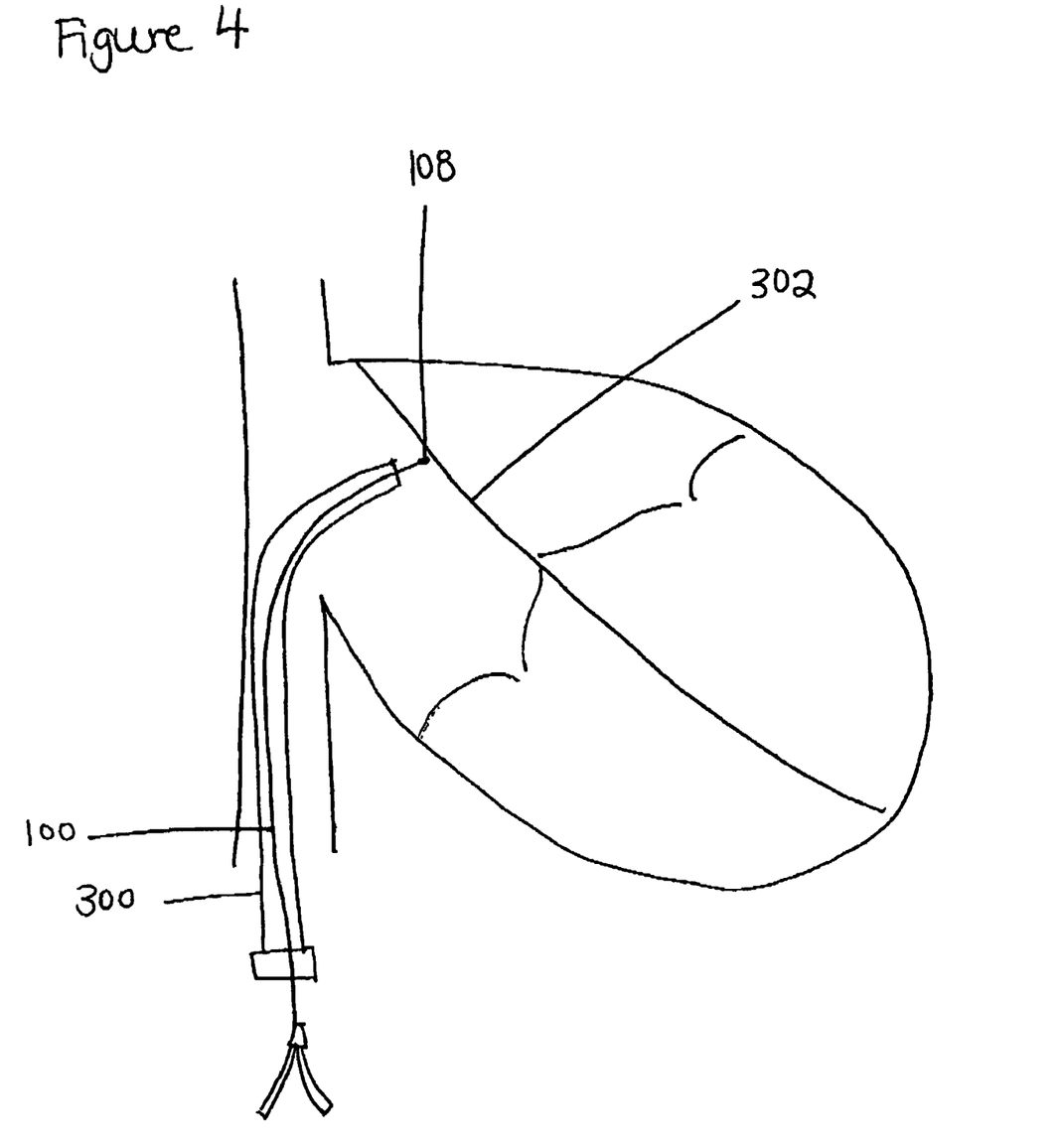
FIG. 4 illustrates a view of the transseptal device of FIG. 1 positioned against an atrial septum.
Figure 5:
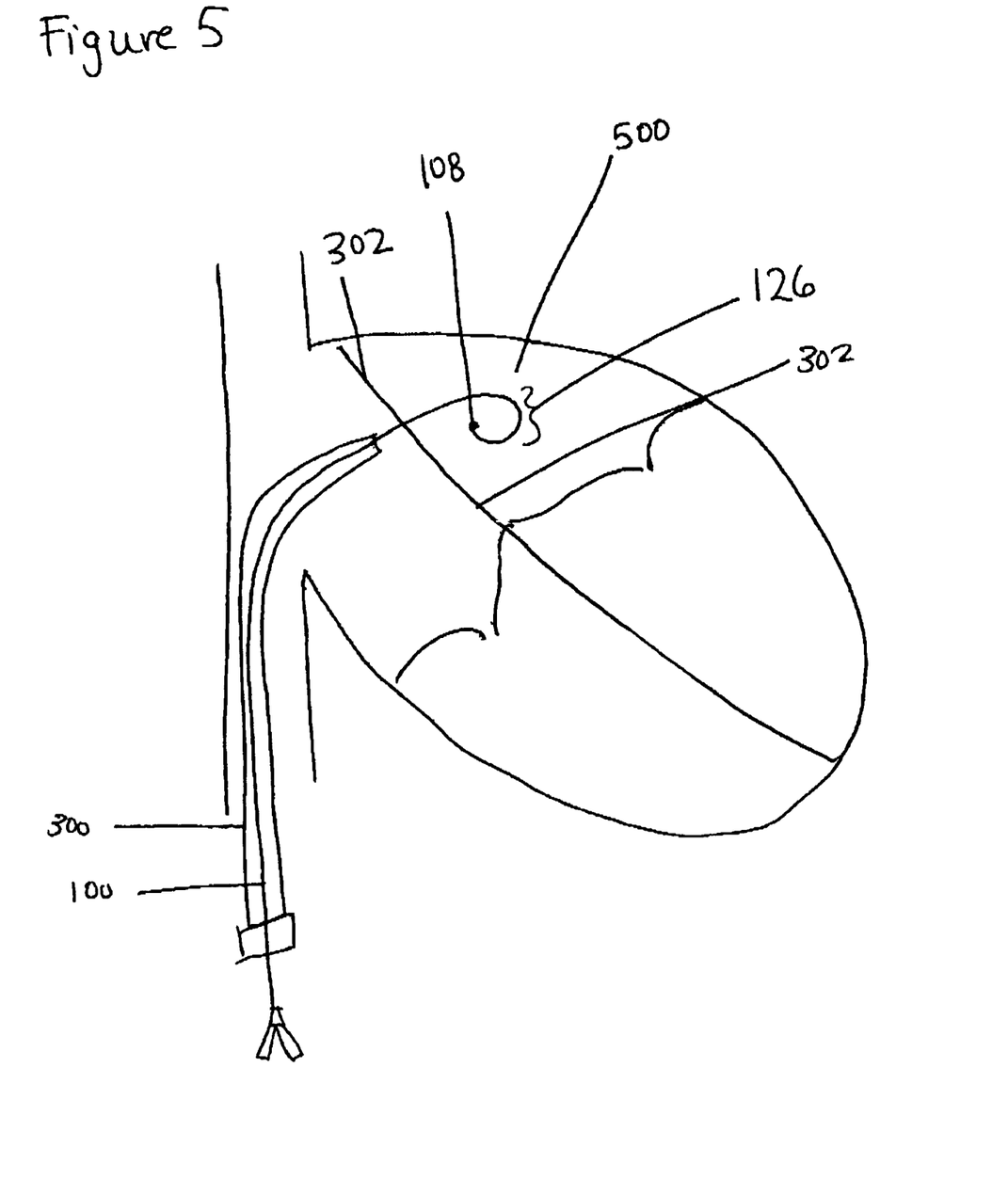
FIG. 5 illustrates a view of the transseptal device of FIG. 1 after perforating the atrial septum and being advanced into the left atrium.

FIG. 2 depicts the curve 126 of the preferred embodiment of the transseptal device 100. Preferably, curve length is approximately 6 cm (about 2.36") and traverses 270 degrees of the circumference of a circle. The curve 126 directs functional tip away from cardiac structures after septal perforation, decreasing the risk of inadvertent cardiac perforation. FIGS. 3, 4 and 5 depict transseptal device 100 during use. The transseptal device 100 is introduced into patient through a guiding catheter 300. Distal region 104 is pliable so that the curve 126 straightens out within guiding catheter 300 and takes on the shape of guiding catheter 300 as it is advanced to the atrial septum 302, as shown in FIG. 3. The transseptal device 100 is longer than the guiding catheter 300 so that it may be advanced slightly out of the tip of guiding catheter 300, exposing functional tip 108, as shown in FIG. 4. Functional tip 108 is positioned against a desired perforation site on atrial septum 302, and energy is delivered to perforate septum 302. In the preferred embodiment curve 126 begins 1 cm (about 0.39") proximal to functional tip 108, leaving a 1 cm (about 0.39") distal portion of the transseptal device 100 straight. This ensures that the transseptal device 100 will exit guiding catheter 300 straight, enabling operator to easily position the transseptal device against septum 302. After the 1 cm (about 0.39") distal portion of the transseptal device 100 has been advanced out of the guiding catheter 300 and across the atrial septum 302, distal region 104 exits guiding catheter 300 and establishes its curved shape within left atrium 500, protecting heart structures from inadvertent injury. In an alternate embodiment, the shape of distal region 104 is modifiable by the operator during use. In this embodiment, distal region 104 is connected to a control (not shown) associated with proximal region 106. The control is typically a lever attached to a cord extending within the transseptal device and attached to the distal region 104. When the lever is moved, tension on cord increases or decreases, and alters the shape of distal region. An operator uses the control to position functional tip 108 in a location within the heart such that inadvertent cardiac injury is unlikely.

Figure 6:
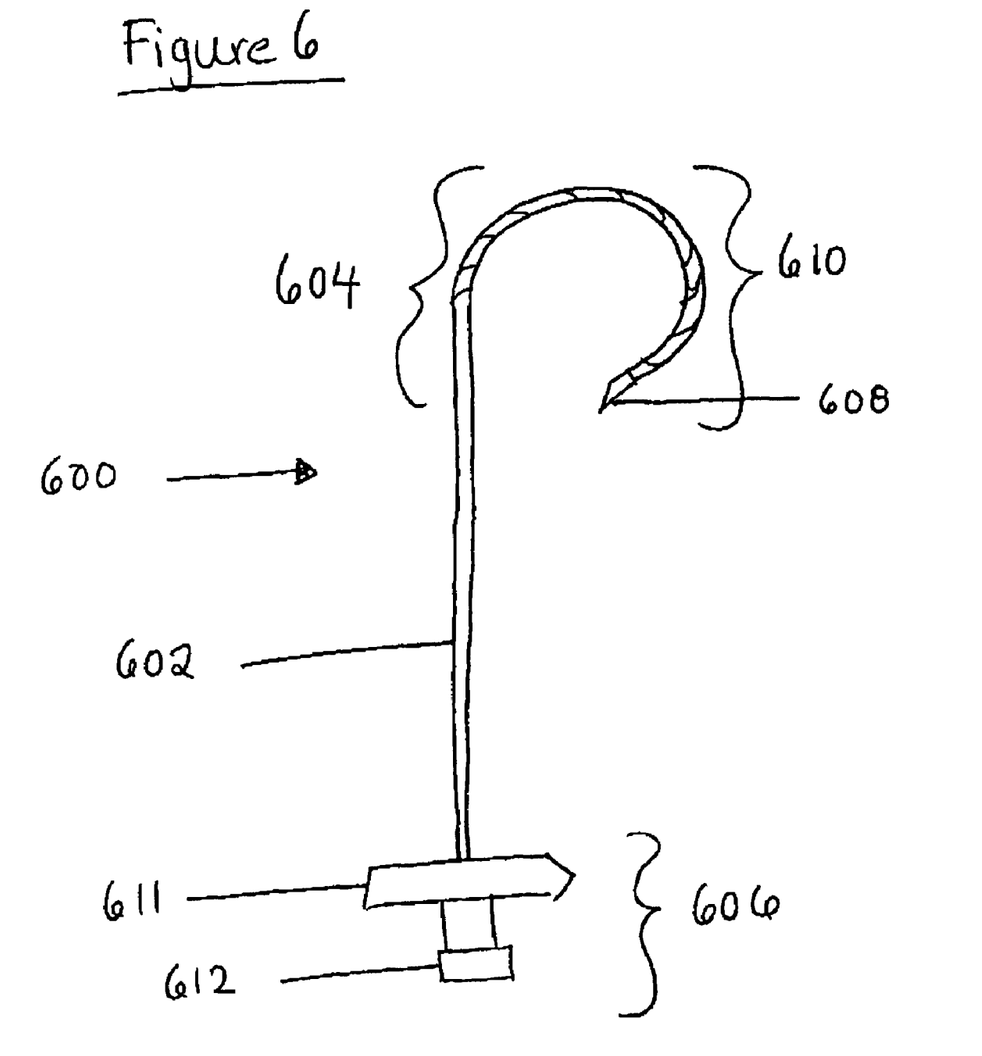
FIG. 6 illustrates an alternate embodiment of the transseptal device in accordance with the invention.

In a further embodiment of a transseptal device 600 as shown in FIG. 6, the energy form used to perforate septum 302 is mechanical. In this embodiment, elongate member 602 is preferably made of a very stiff material such as stainless steel, or a shape-memory metal. The transseptal device 600 comprises a lumen connecting distal region 604 to proximal region 606. Distal region 604 comprises a functional tip 608 configured as a sharp needle tip. When functional tip 108 is in position adjacent septum 302, perforation is achieved by applying a mechanical force to proximal region 606 to push functional tip 608 to cut the septum 302 and create the desired perforation. Distal region 604 comprises a curved portion 610 made of a super-elastic material to enable the curve to straighten when advanced through a guiding catheter. The super-elastic material is preferably a memory metal such as Nitinol. In this embodiment, the transseptal device 600 is made of one continuous metal tube with a sharpened functional tip 608. Curved region 610 begins 1 cm (about 0.39") proximal to the functional tip 608 and continues for approximately 6 cm (about 2.36"). Curved region 610 is preferably ground down to achieve a smaller wall thickness, and its surface about its outer diameter may be etched to increase pliability. The transseptal device 600 is secured in a desired curve shape and exposed to high temperatures to set the desired curve. Proximal region 606 comprises a handle 611 for operator to grip while applying mechanical energy to perforate septum 302, and a hub 612 to connect a pressure monitor or syringe for fluid injection.

Figure 7A:
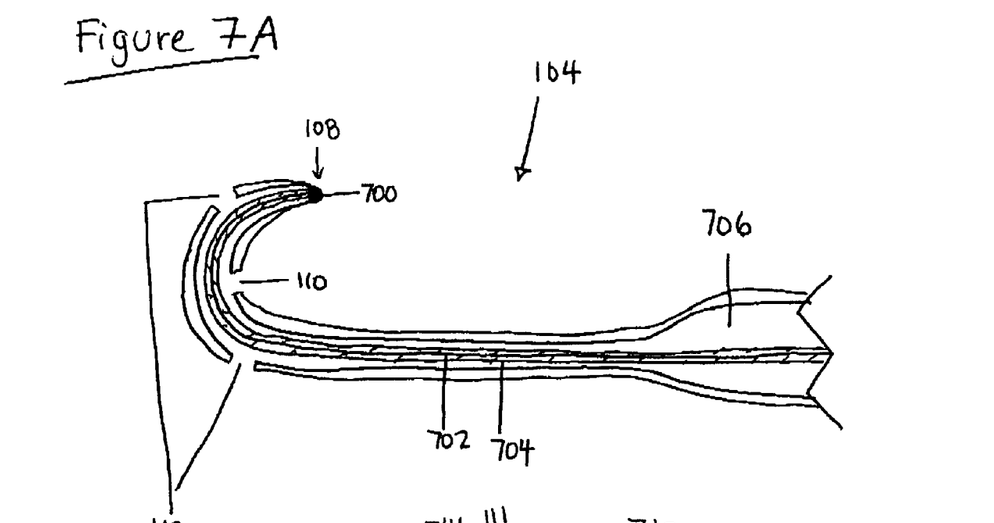
FIGS. 7A and 7B illustrate respectively a side cross-sectional view of the distal and proximal regions of the transseptal device of FIG. 1.
Figure 7B:
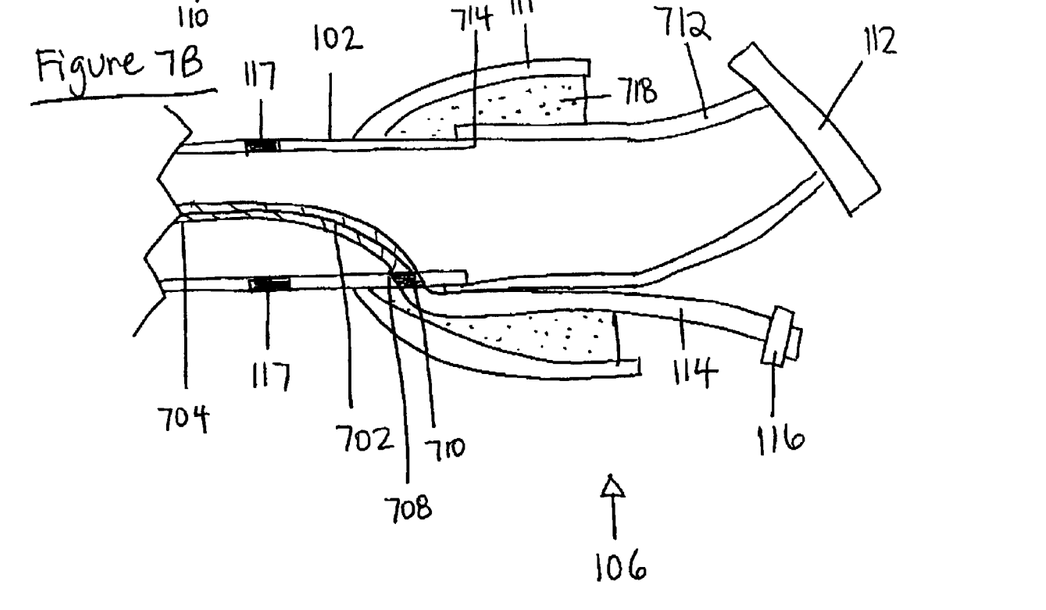

Referring to FIGS. 7A and 7B a cross-section of proximal 106 and distal 104 regions of the transseptal device 100 is illustrated in accordance with the preferred embodiment of FIG. 1. Functional tip 108 comprises an active electrode 700 that is coupled to an electrically insulated conducting wire 702. Conducting wire 702 is preferably attached to distal region 104 using an adhesive. Alternately, distal region 104 is melted onto insulation 704 on conducting wire 702 to form a bond.

Figure 8:
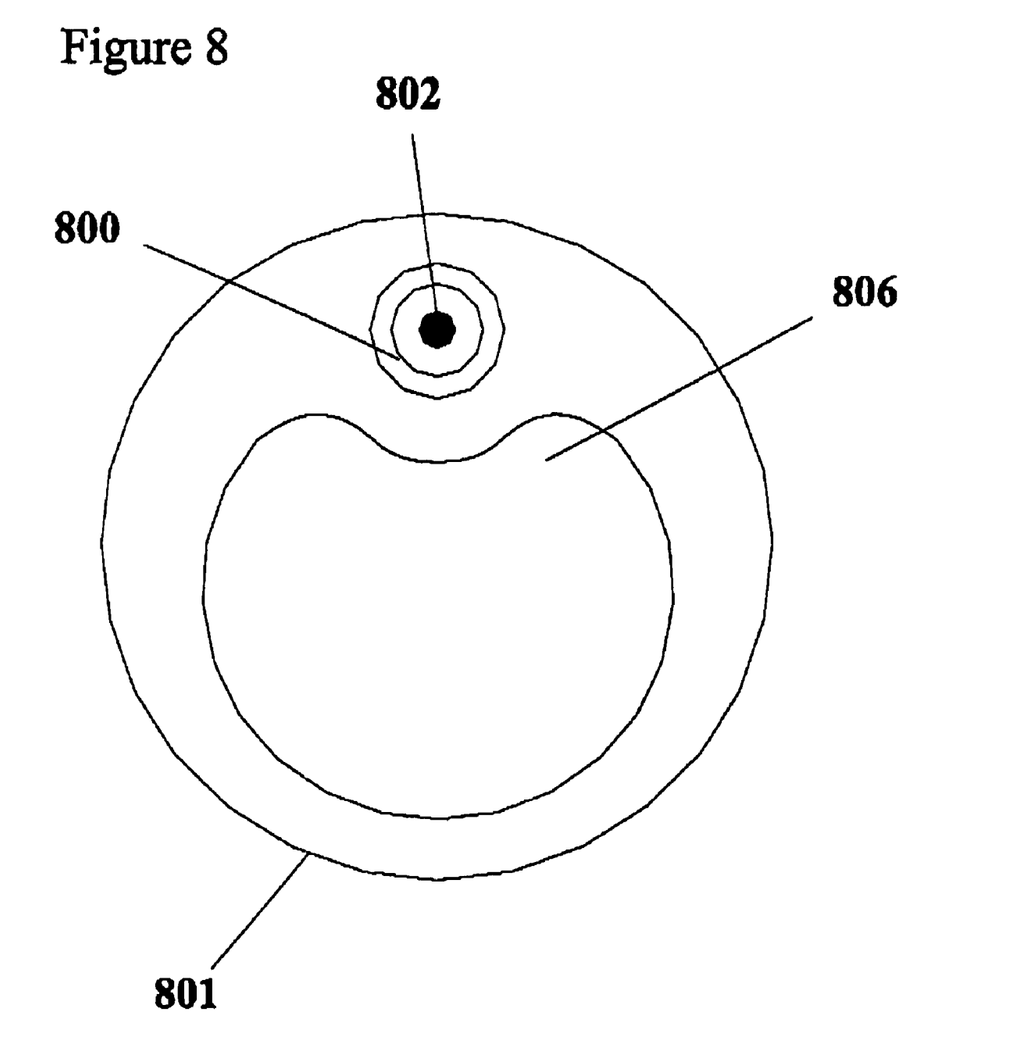
FIG. 8 illustrates a cross-sectional view of an alternate embodiment of the transseptal device.

Conducting wire 702 carries electrical energy from generator 122 to active electrode 700. Conducting wire 702 is covered with insulation 704 made of a biocompatible material that is able to withstand high temperatures such as polytetrafluoroethylene (PTFE), or other insulating material. Conducting wire 702 preferably extends through a main lumen 706 of the transseptal device 100 which lumen extends from proximal region 106 to distal region 104. In an alternate embodiment illustrated in cross-section in FIG. 8, an elongate member 801 comprises a main lumen 806 and a separate lumen 800. Separate lumen 800 contains a conducting wire 802 therein and main lumen 806 is used for aspiration of blood and injection of contrast and other media. This embodiment of elongate member 801 allows a dedicated lumen for each function of the transseptal device 100.

In the preferred embodiment of FIGS. 7A and 7B, main lumen 706 extends from distal region 106 along elongate member 102 and through distal region 104 of the transseptal device 100. At least one opening 110 at the distal region 104 provides a pathway between main lumen 706 and the environment surrounding distal region 104, such as a desired location within a patient's body. Openings 110 are sufficiently dimensioned to easily aspirate blood and to inject radiopaque contrast to and through main lumen 706; however, openings 110 are limited in number and dimension so that they do not compromise the structural integrity of distal region 104. The location of openings 110 is as close to functional tip 108 as possible so that only a small portion of the transseptal device 100 is required to be proximate to the desired location for the determination of pressure.

Hub 112 is configured for releaseably coupling to an external pressure transducer 118, or a standard syringe. Preferably, hub 112 comprises a female luer lock connection. Hub 112 is coupled to main lumen 706 via tubing 712 to provide a pathway from main lumen 706 to external pressure transducer 118 so that blood pressure can be determined using a method that is known to those of ordinary skill in the art. Conducting wire 702 exits elongate member 102 through an exit point 708. Exit point 708 is sealed with an adhesive or a polymeric material. Conducting wire 702 is electrically coupled to cable 114 by a joint 710. This joint can be made by soldering, or another wire joining method known to persons of ordinary skill in the art. Cable 114 terminates with a connector 116 that can mate with either the generator 122, or a separate extension connector cable (not shown). Cable 114 and connector 116 are made of materials suitable for sterilization, and will insulate the user from energy travelling through the conductor.

Elongate member 102 is coupled to tubing 712 at proximal end 714 of member 102. Tubing 712 is made of a polymeric material that is more flexible than member 102. A suitable material for tubing is polyvinylchloride (PVC), or another flexible polymer. Tubing 712 is coupled to hub 112. This configuration provides a flexible region for the user to handle when releaseably coupling external pressure transducer 118, or other devices to hub 112. Couplings between member 102 and tubing 712, and tubing 712 and hub 112 are made with an adhesive such as a UV curable adhesive, an epoxy, or another type of adhesive.

A handle 111 surrounds the joint 710 and the proximal end of member 714 in order to conceal these connections. Handle 111 is made of a polymeric material, and is filled with a filling agent 718 such as an epoxy, or another polymeric material in order to hold the cable 114 and the tubing 712 in place.

Figure 9:
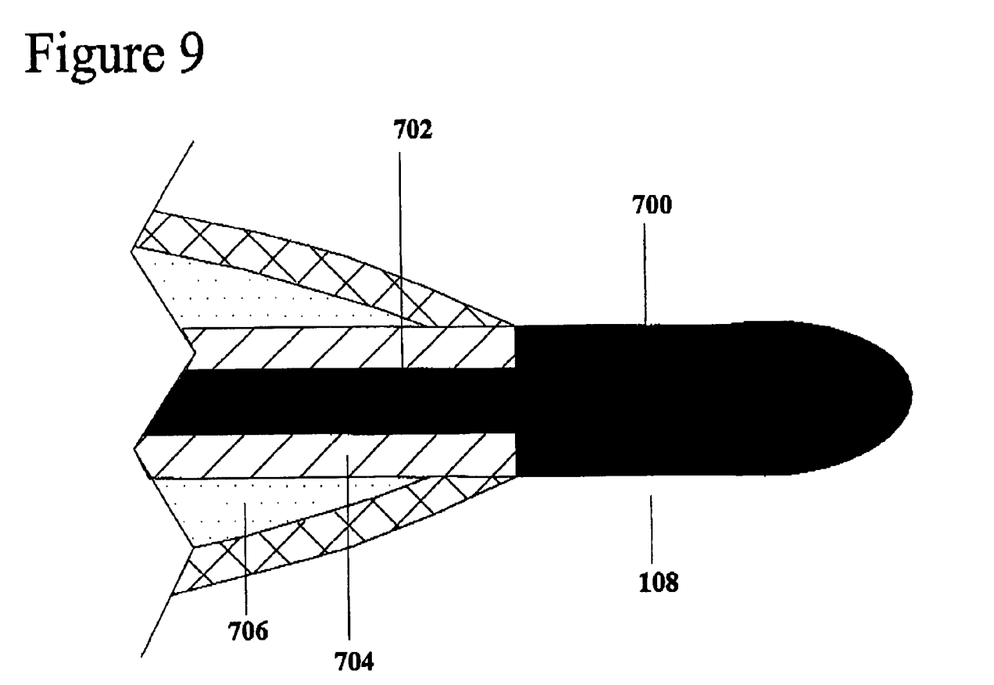
FIG. 9 illustrates a side cross-sectional view of a functional tip of the transseptal device of FIG. 1.

Referring to FIG. 9 there is illustrated a view of a preferred embodiment of functional tip 108. Functional tip 108 comprises one active electrode 700 configured in a bullet shape. Active electrode 700 is preferably 0.059" (0.15 cm) long and preferably has an outer diameter of 0.016" (0.04 cm). Active electrode 700 is coupled to an end of the conducting wire 702, also made out of a conductive and radiopaque material. RF energy is delivered through the active electrode 700 to tissue, and travels through the patient to the grounding pad 124, which is connected to the generator 122. Alternate embodiments of an active electrode are configured in shapes other than a bullet. These shapes include a spherical shape, a rounded shape, a ring shape, a semi-annular shape, an ellipsoid shape, an arrowhead shape, a spring shape, a cylindrical shape, among others.

Figure 10:
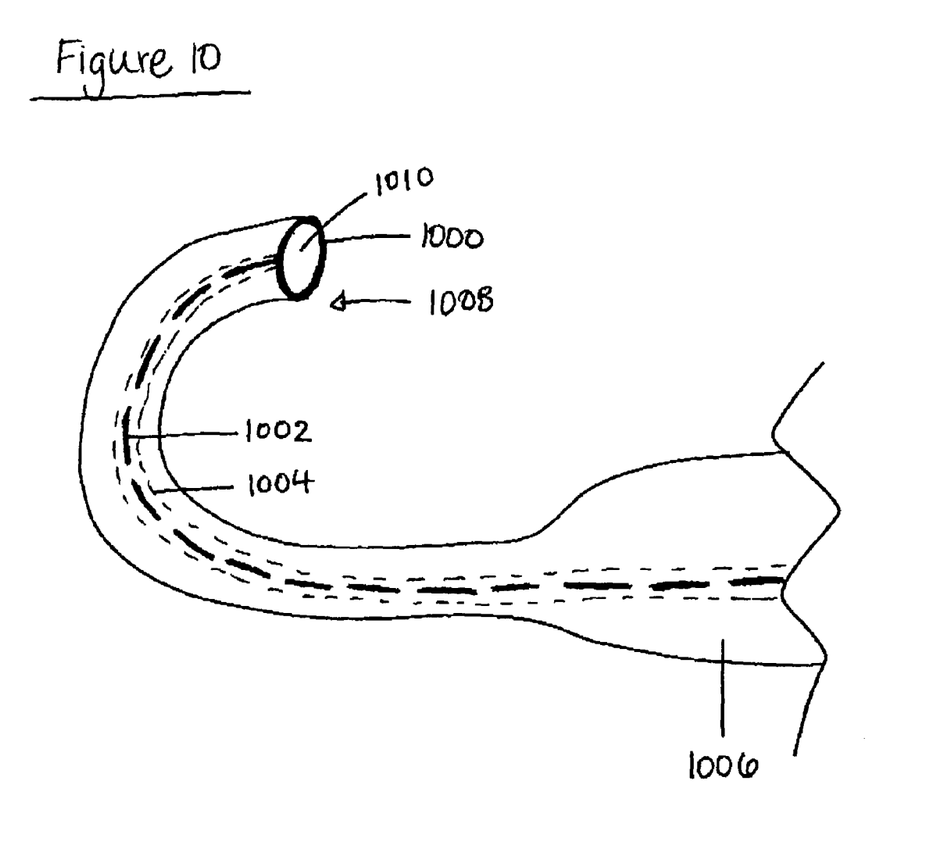
FIG. 10 illustrates a side cross-sectional view of an alternate embodiment of a distal region of a transseptal device in accordance with the invention.

Referring to FIG. 10 there is illustrated an alternate embodiment of a functional tip 1008. Functional tip 1008 comprises one active electrode 1000 in a ring configuration. Conducting wire 1002 is coupled to the active electrode 1000, and active electrode 1000 is positioned around a perimeter of a single opening 1010 that provides a pathway between main lumen 1006 and a patient's body. Another similar embodiment to a functional tip comprises an active electrode in a partially annular shape (not shown). In other embodiments (not shown), functional tip comprises multiple electrodes. Such electrodes may operate in a monopolar mode as with the embodiments detailed in FIGS. 7A, 7B and 10. Otherwise, such electrodes are arranged such that the RF energy is delivered through at least one active electrode at functional tip, and returns to the generator through at least one return electrode at functional tip. The use of an active and a passive electrode on board the transseptal device 100 eliminates the need for a grounding pad 124 to be attached to the patient as is well understood by persons of ordinary skill in the art.

In the preferred embodiment, external pressure transducer 118 is releaseably coupled to the transseptal device 100. Hub 112 is coupled to external tubing 119 that is coupled to external pressure transducer 118 as shown in FIG. 1. External tubing 119 is flushed with saline to remove air bubbles. When the transseptal device 100 is positioned in a blood vessel in a body, pressure of fluid at distal region 104 exerts pressure through openings 110 on fluid within main lumen 706, which exerts pressure on saline in the external tubing 119, which exerts pressure on the external pressure transducer 118. The at least one opening 110 and the main lumen 706 provide a pressure sensing mechanism in the form of a pressure transmitting lumen for coupling to pressure transducer 118. External pressure transducer 118 produces a signal that varies as a function of the pressure it senses. External pressure transducer 118 is also releaseably electrically coupled to a pressure monitoring system 120 that converts the transducer's signal and displays a pressure contour as a function of time.

Figure 11:
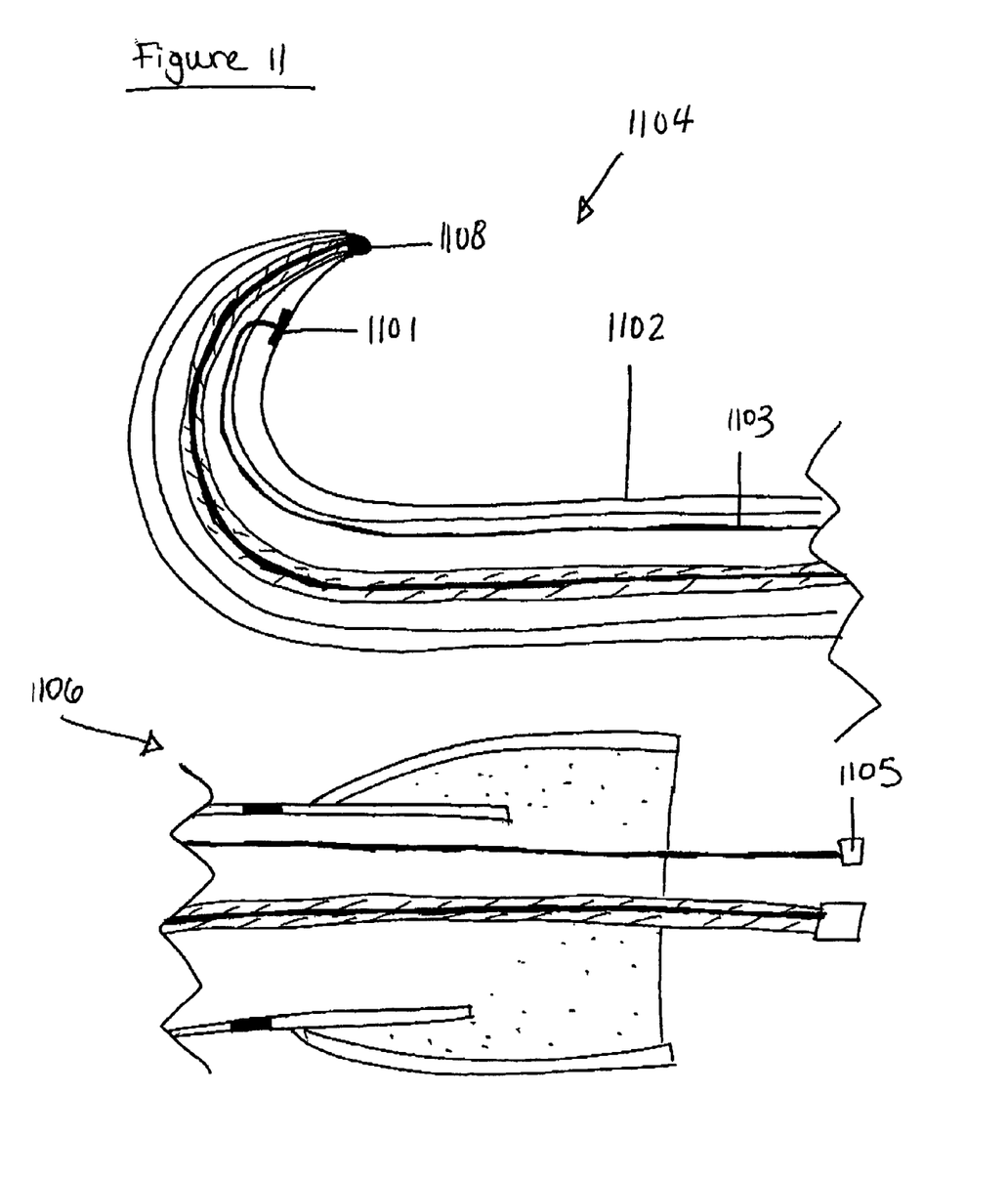
FIG. 11 illustrates a side cross-sectional view of an alternate embodiment of the distal and proximal regions of a transseptal device.

Referring to FIG. 11 there is illustrated an alternate embodiment of a transseptal device 1100 that does not use an external pressure transducer 118 as in the embodiment of FIG. 1. In the embodiment of FIG. 11 the pressure sensing mechanism comprises an on-board pressure transducer 1101 coupled by an adhesive to elongate member 1102 at distal region 1104. Pressure transducer 1101 is configured at distal region 1104 such that pressure close to functional tip 1108 can be transduced. The on-board pressure transducer 1101 is electrically coupled to a pressure communicating cable 1103 to provide power to the pressure transducer 1101 and to carry a pressure signal to proximal region 1106 of the transseptal device 1100. The pressure communicating cable 1103 terminates in a monitoring system connector 1105 that is configured to be releaseably coupled to a pressure monitoring system 120. Monitoring system 120 converts the pressure signal and displays pressure as a function of time. In the embodiment of FIG. 11, a main lumen is not required for fluid communication with an external pressure transducer. In addition, this embodiment does not require openings at distal region 106 for fluid communication with a main lumen. However, a lumen with openings may be provided for injecting or aspirating fluids, if desired.

The present invention thus provides a device that is capable of creating a perforation in the atrial septum while minimizing the risk of inadvertent cardiac injury. The perforation is created by the application of energy to a functional tip on the transseptal device. A preferred means for minimizing the risk of inadvertent injury comprises a curve at the distal end of the transseptal device. In the preferred embodiment, there is at least one opening near the distal region of the transseptal device for blood or other fluid to enter and fill the lumen and exert a measurable pressure on a coupled external transducer. The lumen and opening may also be useful for injecting radiopaque contrast or other agents through the transseptal device.

The transseptal device of the invention is useful as a substitute for a traditional transseptal needle to create a transseptal perforation. The transseptal device of the present invention preferably has a soft and curved distal region with a functional tip that uses RF energy to create a perforation across a septum, making the procedure more easily controlled and less operator dependent than a transseptal needle procedure. The soft distal region of the transseptal device reduces incidents of vascular trauma as the transseptal device is advanced through the vasculature. The application of RF energy is controlled via an electric generator, eliminating the need for the operator to subjectively manage the amount of force necessary to cross the septum with a traditional needle. The present invention eliminates the danger of applying too much mechanical force and injuring the posterior wall of the heart.

In an alternate embodiment, the transseptal device is a metal needle with a curved distal end. In this embodiment the operator applies mechanical energy to perforate the septum, however because the transseptal device curls in the left atrium the risk of inadvertent cardiac injury is minimized.

The preferred embodiment of this invention is intended to be used to create a perforation in the atrial septum of a patient, however it could also be used in other locations within the heart such as the ventricular septum, or one of the valves. In addition, it could be used in other medical applications where a perforation is required. Applications may include perforating through occluded conduits within the body including but not limited to arteries and veins. Alternately, it could be used for perforating through organs in order to gain access to other areas in the body.

Although the above description relates to specific embodiments as presently contemplated by the inventors, it is understood that the invention in its broad aspect includes mechanical and functional equivalents of the elements described herein. The embodiment(s) of the invention described above is(are) intended to be exemplary only. The scope of the invention is therefore intended to be limited solely by the scope of the appended claims.

What is claimed is:

1. A method of creating a perforation in a heart septum comprising the steps of:
   applying a form of energy to a perforation device positioned at a desired location of a heart septum to create a perforation at said desired location, wherein said perforation device comprises an elongate member having a proximal region and a distal region and wherein said distal region comprises a portion fixed in a desired curve shape; and
   advancing a distal tip of the device through the septum, such that said distal tip is automatically directed away from cardiac structures while being advanced, due to the shape of the curved portion;
   whereby said distal tip is directed away from said cardiac structures in order to decrease risk of unwanted injury.

2. The method of claim 1 wherein said perforation device comprises a pressure sensing mechanism for sensing pressure at said distal tip and wherein the method comprises monitoring said pressure to indicate a location of said distal tip.

3. The method of claim 1 wherein said perforation device comprises an orientation indicator for determining a direction of said distal tip and wherein the method comprises monitoring said orientation indicator to advance said distal tip through said septum in a desired direction.

4. The method as claimed in claim 1, further comprising the steps of inserting said perforation device into a guiding catheter and advancing said perforation device through said guiding catheter within a patient's vasculature, wherein said distal region conforms to a shape of said guiding catheter when inserted into said guiding catheter.

5. The method as claimed in claim 4, wherein said distal region further comprises a substantially straight portion distal to said curved portion and wherein the method comprises a further step of advancing said substantially straight portion of said distal region out of a tip of said guiding catheter in order to position said device at said desired location for creating a perforation.

6. The method as claimed in claim 1 wherein the energy is in the form of electrical current energy in the radio frequency range and wherein the energy is applied to ionize a conductive medium on top of a target tissue resulting in a low temperature molecular disintegration.

7. The method as claimed in claim 1, wherein the energy is in the form of mechanical energy and wherein said perforation device comprises a sharp distal tip.

8. The method as claimed in claim 1 wherein said desired location comprises cellular tissue and wherein sufficient energy is delivered to the tissue so as to cause cell lysis to occur.

* * * * *